US00PP16852P2

(12) United States Plant Patent
Boeder

(10) Patent No.: US PP16,852 P2
(45) Date of Patent: Jul. 18, 2006

(54) ***CHRYSANTHEMUM* PLANT NAMED 'CEKIWI GREEN'**

(50) Latin Name: *Chrysanthemum morifolium*
Varietal Denomination: Cekiwi Green

(75) Inventor: Mark Roland Boeder, The Hague (NL)

(73) Assignee: Chrysanthemum Breeders Association N.V., Aalsmeer (NL)

( * ) Notice: Subject to any disclaimer, the term of this patent is extended or adjusted under 35 U.S.C. 154(b) by 0 days.

(21) Appl. No.: 11/128,376

(22) Filed: May 13, 2005

(51) Int. Cl.
*A01H 5/00* (2006.01)

(52) U.S. Cl. ..... Plt./287

(58) Field of Classification Search ..... Plt./287
See application file for complete search history.

*Primary Examiner*—Kent Bell
*Assistant Examiner*—Annette H Para
(74) *Attorney, Agent, or Firm*—Steptoe & Johnson LLP

(57) ABSTRACT

A *Chrysanthemum* plant named 'Cekiwi Green' characterized by its small sized pompon type blooms with green ray-florets, with a response time of 49 days.

3 Drawing Sheets

BACKGROUND OF THE INVENTION

'Cekiwi Green' is a product of a breeding-program which had the objective of creating new *chrysanthemum* cultivars with a pompon type flower, a 7 week response and a medium plant height (90 cm). The new plant of the present invention comprises a new and distinct cultivar of *Chrysanthemum* plant. 'Cekiwi Green' is a seedling from a cross in a breeding program maintained under the control of inventor. The female parent is #2678—unpatented—, an unnamed seedling not available to inventor for description. The male parent is unknown, being a mixed population of a group of male parents. The new and distinct cultivar was discovered and selected as a flowering plant within the progeny of the stated cross by Mark Roland Boeder in a controlled environment (greenhouse) in Rijsenhout, The Netherlands in 2001. The first act of asexual reproduction of 'Cekiwi Green' was accomplished when vegetative cuttings were taken from the initial selection in 2001 and propagated further in a controlled environment in Rijsenhout, The Netherlands.

SUMMARY OF THE INVENTION

The present invention is a new and distinct variety of *chrysanthemum* bearing small sized green pompon type blooms.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
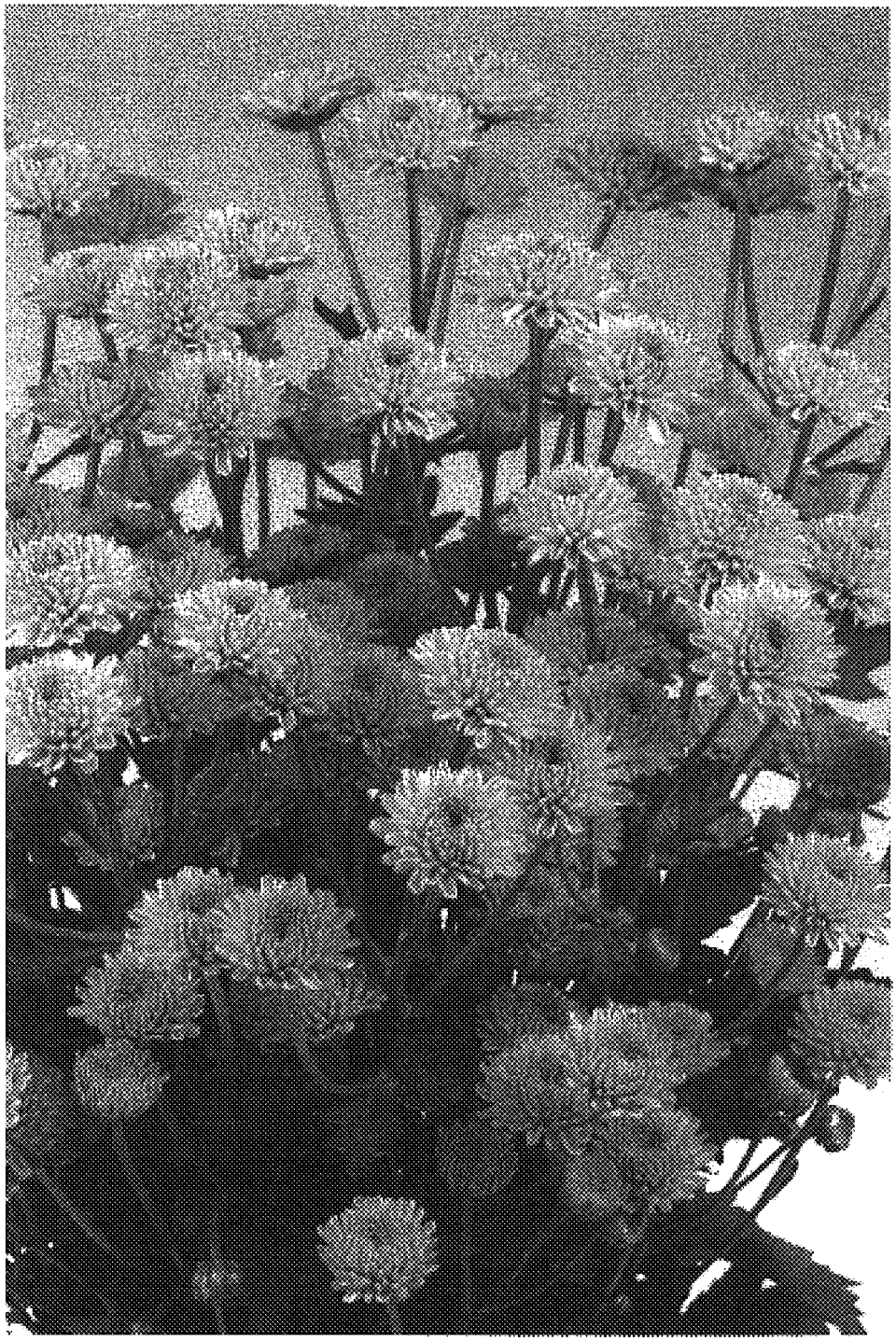
FIG. 1 shows a plant of the cultivar in full bloom.
Figure 2:
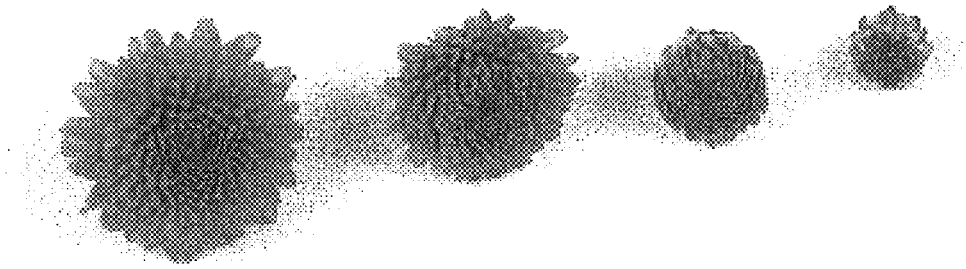
FIG. 2 shows the various stages of bloom of the new cultivar.
Figure 3:
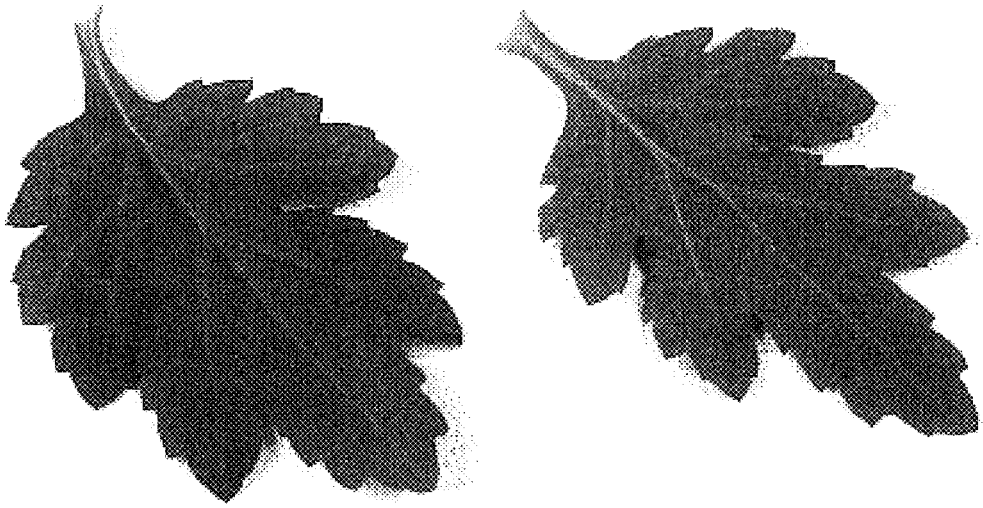
FIG. 3 shows the foliage of the new cultivar.

This new variety of *chrysanthemum* is of the botanical classification *Chrysanthemum morifolium*. The observations and measurements were gathered from plants grown in April/May in a greenhouse in Rijsenhout, The Netherlands in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 49 days. After the long day period to flowering growth retardants were applied 2 to 3 times in an average dose of 2.5 gram/liter water. The plants were observed (directly) during the flowering of this crop. This variety is sensitive to infection by white rust and infestation by the insect Western flower thrips and leafminer. No tests were done on disease or insect resistance or susceptibility. No tests were done on cold or drought tolerance. This new variety produces small sized blooms with green ray-florets blooming on the plant for 1 week. This new variety of *chrysanthemum* has been found to retain its distinctive characteristics throughout successive propagations however the phenotype may vary significantly with variations in environment such as light intensity and temperature. To show the phenotype as described 'Cekiwi Green' can be planted with assimilation lightning (high pressure sodium lamps; minimal level 2500 lux) all year round under greenhouse conditions in The Netherlands.

From the cultivars known to inventor the most similar existing cultivar in comparison to 'Cekiwi Green' is 'Yoko Ono' (U.S. Plant Pat. No. 12,566). When 'Yoko Ono' and 'Cekiwi Green' are being compared the following differences and similarities are noticed: Both 'Yoko Ono' and 'Cekiwi Green' have green pompon type flowers. The differences of 'Yoko Ono' and 'Cekiwi Green' are (1) Colour ray florets. The colour of the flowers of 'Cekiwi Green' is more deep green than that of 'Yoko Ono' (2) Length peduncles. The peduncles of 'Cekiwi Green' are longer than those of 'Yoko Ono'. (3) Plant vigour. The plants of 'Cekiwi Green' show a very strong vigour, whereas those of 'Yoko Ono' are moderately vigorous.

The following is a description of the plant and characteristics that distinguish 'Cekiwi Green' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

Botanical Description of variety 'Cekiwi Green'

| | |
|---|---|
| **Bud** | |
| Size | Small, cross-section 0.8 cm height 0.5 cm |
| Outside color | Green 143 C |
| Phyllaries | 2 rows, length 7 mm, width 3 mm |
| Phyllaries among disc-florets | Not present |
| Phyllaries color | Green 138 B |
| **Inflorescence** | |
| Type | Double; Pompon |
| Height | 1.5 cm |
| Size | Small |
| Fully expanded | 3.5 cm |
| Number of blooms per stem | Average of 17 |
| Performance on the plant | 1 week |
| Seeds (if crossed) | Produced in very small quantities, oval shaped, grey-brown 199 A, 2 mm in length. |
| Fragrance | Typical *chrysanthemum,* slight |
| Peduncle length | Near the top 6 cm, near the middle 15 cm, near the bottom 22 cm |
| Peduncle color | Green 143 A–B |
| **Color** | |
| Color of the ray-florets | Upper surface Green 143 C<br>Lower surface Yellow-green 144 C |
| Tonality from Distance | A spray mum with green pompon type flowers |
| Color of the upper surface of the ray-florets after aging of the plant | Green 143 D |
| **Ray florets** | |
| Texture | Upper and under side smooth |
| Number | 240–260 |
| Cross section | Convex |
| Longitudinal axis of majority | Straight |
| Length of corolla tube | 0.3 cm |
| Ray-floret margin | Entire |
| Ray-floret length | 1.5 cm |
| Ray-floret width | 0.2 cm |
| Ratio length/width | High |
| Shape of tip | Round |
| Disc florets | Absent |
| Receptacle shape | Domed raised |
| **Reproductive Organs** | |
| Stamen | Absent |
| Pollen | Not produced |
| Styles | Present in ray florets |
| Style color | Yellow 13 A |
| Style Length | 3 mm |
| Stigma color | Yellow-green 145 D |
| Stigma Width | 1 mm |
| Ovaries | Enclosed in perianth |

TABLE 1-continued

Botanical Description of variety 'Cekiwi Green'

| | |
|---|---|
| **Plant** | |
| Form | A spray mum meant for erect culture |
| Growth habit | Upright |
| Growth rate | Very strong |
| Height | 90 cm |
| Width | 15 cm |
| Internode length | 2–3 cm |
| Spray formation | Corymbiform |
| Stem Color | Green 138 A |
| Stem Strength | Strong |
| Stem Brittleness | Brittle |
| Stem Anthocyanin coloration | Absent |
| Flowering Response (photo-periodic controlled crop, not natural season) | 49 days (summer) to 57 days (winter) |
| **Foliage** | |
| Color immature stage | Upper side Green 143 A–B<br>Under side Green 139 C |
| Color mature stage | Upper side Green 139 A–B<br>Under side Green 139 C |
| Color midvein mature leaf | Upper side Yellow-green 145 C<br>Under side Yellow-green 147 D |
| Size | Medium; length 9–11 cm, width 4.5–6 cm |
| Quantity (number per single stem) | 26–28 |
| Shape | Elliptic |
| Texture upper side | Fleshy and glabrous |
| Texture under side | Pubescent |
| Venation arrangement | Palmate |
| Shape of the margin | Serrate |
| Shape of Base of Sinus Between Lateral Lobes | Rounded |
| Margin of Sinus Between Lateral Lobes | Diverging |
| Shape of Base | Truncate |
| Apex | Mucronulate |
| Petiole Length | 1.5 cm |
| Petiole Color | Yellow-green 145 C |

TABLE 2

Differences with comparison variety

| | 'Cekiwi Green' | 'Yoko Ono' |
|---|---|---|
| Colour ray-florets | Green 143 C | Yellow-green 145 A to 154 A |
| Length peduncles | 6–22 cm | 1.5–7 cm |
| Plant vigour | Very strong | Moderate |

I claim:

1. A new and distinct variety of *chrysanthemum* plant as described and illustrated.

* * * * *